US010004841B2

(12) United States Patent
Larson et al.

(10) Patent No.: US 10,004,841 B2
(45) Date of Patent: Jun. 26, 2018

(54) BLOOD PURIFIER DEVICE AND METHOD

(71) Applicants: Michael C. Larson, Wauwatosa, WI (US); Bonnie P. Freudinger, Milwaukee, WI (US)

(72) Inventors: Michael C. Larson, Wauwatosa, WI (US); Bonnie P. Freudinger, Milwaukee, WI (US)

( * ) Notice: Subject to any disclaimer, the term of this patent is extended or adjusted under 35 U.S.C. 154(b) by 630 days.

(21) Appl. No.: 14/565,033

(22) Filed: Dec. 9, 2014

(65) Prior Publication Data

US 2015/0158033 A1 Jun. 11, 2015

Related U.S. Application Data

(60) Provisional application No. 61/913,649, filed on Dec. 9, 2013.

(51) Int. Cl.
*A61M 1/36* (2006.01)
*B03C 5/02* (2006.01)

(52) U.S. Cl.
CPC ............... *A61M 1/36* (2013.01); *B03C 5/026* (2013.01); *A61M 2205/054* (2013.01); *B03C 2201/26* (2013.01)

(58) Field of Classification Search
CPC .......... A61M 1/34–1/3698; C02F 1/46–1/488; B01D 35/06; B03C 5/02–5/028
See application file for complete search history.

(56) References Cited

U.S. PATENT DOCUMENTS

| 3,328,255 | A | | 6/1967 | Ilg |
| 3,608,088 | A | * | 9/1971 | Dorman et al. ...... F04D 13/026 |
| | | | | 128/899 |
| 3,640,388 | A | | 2/1972 | Ferrari |
| 3,674,271 | A | * | 7/1972 | De Gelder ............... A63H 1/00 |
| | | | | 273/115 |
| 4,038,194 | A | | 7/1977 | Luceyk et al. |
| 4,038,197 | A | | 7/1977 | Caspari |
| 4,053,420 | A | | 10/1977 | Marx |
| 4,091,989 | A | | 5/1978 | Schlultz |
| 4,453,927 | A | | 6/1984 | Sinko |
| 4,668,214 | A | | 5/1987 | Reeder |

(Continued)

FOREIGN PATENT DOCUMENTS

| EP | 0 056 137 A2 | 7/1982 |
| EP | 0 745 397 A2 | 4/1996 |

(Continued)

*Primary Examiner* — Bryan D. Ripa
*Assistant Examiner* — Ho-Sung Chung
(74) *Attorney, Agent, or Firm* — Andrus Intellectual Property Law, LLP (57) ABSTRACT

Embodiments of the invention provide a gravity-fed blood purifier device for removing waste particles from blood. In one embodiment, the blood purifier device includes a pair of end plates and a first cylindrical tube located between the end plates. The blood purifier device also includes a porous tube contained within the space defined by the first cylindrical tube. An inlet provides unpurified red blood cells into blood purifier device. An electrode generates a negative potential across the porous tube to repel red blood cells so that the waste particles pass through the porous tube and the red blood cells do not. An outlet can be coupled to one of the end plates to receive the purified red blood cells.

21 Claims, 11 Drawing Sheets

(56) References Cited

U.S. PATENT DOCUMENTS

| | | | |
|---|---|---|---|
| 4,767,397 A | 8/1988 | Hohenberg et al. | |
| 4,946,603 A | 8/1990 | Laugharn et al. | |
| 5,059,654 A | 10/1991 | Hou et al. | |
| 5,114,396 A | 5/1992 | Unger et al. | |
| 5,131,994 A | 7/1992 | Shmidt et al. | |
| 5,185,086 A * | 2/1993 | Kaali | A61K 41/0019 204/164 |
| 5,188,738 A * | 2/1993 | Kaali | A61L 2/0011 204/164 |
| 5,190,657 A | 3/1993 | Heagle et al. | |
| 5,192,439 A | 5/1993 | Roth et al. | |
| 5,277,820 A | 1/1994 | Ash | |
| 5,298,016 A | 3/1994 | Gordon | |
| 5,456,835 A | 10/1995 | Castino et al. | |
| 5,647,976 A * | 7/1997 | Rothe | B01D 11/0203 210/137 |
| 5,652,148 A | 7/1997 | Doshi et al. | |
| 5,660,798 A | 8/1997 | Doshi et al. | |
| 5,766,552 A | 6/1998 | Doshi et al. | |
| 5,919,369 A | 7/1999 | Ash | |
| 6,027,441 A | 2/2000 | Cantu et al. | |
| 6,036,857 A | 3/2000 | Chen et al. | |
| 6,099,491 A | 8/2000 | Headley et al. | |
| 6,129,848 A | 10/2000 | Chen et al. | |
| 6,132,607 A | 10/2000 | Chen et al. | |
| 6,217,540 B1 | 4/2001 | Yazawa et al. | |
| 6,251,291 B1 | 6/2001 | Lamphere et al. | |
| 6,274,041 B1 | 8/2001 | Williamson et al. | |
| 6,287,516 B1 | 9/2001 | Matson et al. | |
| 6,315,706 B1 | 11/2001 | Unger et al. | |
| 6,524,231 B1 | 2/2003 | Westberg et al. | |
| 6,537,614 B1 | 3/2003 | Wei et al. | |
| 6,573,205 B1 | 6/2003 | Myers et al. | |
| 6,582,349 B1 | 6/2003 | Cantu et al. | |
| 6,612,447 B1 | 9/2003 | Breillatt, Jr. et al. | |
| 6,652,475 B1 | 11/2003 | Sahines et al. | |
| 6,673,447 B2 | 1/2004 | Wei et al. | |
| 6,780,327 B1 | 8/2004 | Wu et al. | |
| 6,817,984 B2 | 11/2004 | Robinson et al. | |
| 6,849,185 B1 | 2/2005 | Wu et al. | |
| 6,878,127 B2 | 4/2005 | Brady et al. | |
| 7,033,512 B2 | 4/2006 | Hlavinka et al. | |
| 7,063,816 B2 | 6/2006 | Maianti et al. | |
| 7,166,217 B2 | 1/2007 | Holmes et al. | |
| 7,241,281 B2 | 7/2007 | Coelho et al. | |
| 7,300,413 B2 | 11/2007 | Burbank et al. | |
| 7,438,679 B2 | 10/2008 | Hlavinka et al. | |
| 7,534,348 B2 | 5/2009 | Reitz et al. | |
| 7,780,619 B2 | 8/2010 | Brugger et al. | |
| 8,016,736 B2 | 9/2011 | Hlavinka et al. | |
| 8,105,487 B2 | 1/2012 | Fulkerson et al. | |
| 8,114,288 B2 | 2/2012 | Robinson et al. | |
| 2002/0020675 A1 * | 2/2002 | Herrington | B01D 61/04 210/748.2 |
| 2002/0072129 A1 * | 6/2002 | Poirier | A61M 1/3679 436/520 |
| 2003/0211927 A1 | 11/2003 | Cantu et al. | |
| 2006/0016747 A1 | 1/2006 | Sakaino et al. | |
| 2010/0252435 A1 | 10/2010 | Weber | |

FOREIGN PATENT DOCUMENTS

| | | | |
|---|---|---|---|
| EP | 1 618 940 A1 | 1/2006 | |
| EP | 2446908 A1 * | 5/2012 | A61M 1/1696 |

* cited by examiner

BLOOD PURIFIER DEVICE AND METHOD

CROSS-REFERENCE TO RELATED APPLICATION

The present application is based on and claims priority to U.S. Provisional Patent Application Ser. No. 61/913,649 filed Dec. 9, 2013, the disclosure of which is incorporated herein by reference.

STATEMENT REGARDING FEDERALLY SPONSORED RESEARCH

This invention was made with government support under 1U54HL090503-01 awarded by the National Institute of Health. The government has certain rights to the invention.

BACKGROUND

Red blood cells (RBCs) are specialized cells whose primary role is to deliver oxygen. Approximately 95% of protein in RBCs is hemoglobin, which is the iron-containing protein that binds oxygen in the lungs, and releases it in the rest of the body where it is needed. RBCs obtained from donated blood are essential to modern medical care. Nearly 15 million blood units are transfused every year in U.S. and about 85 units million globally.

While donor blood is important, like any other intervention, it has side effects and limits to its utility. First, blood units contain residual donor antibodies (i.e., alloantibodies) that can increase inflammation and worsen outcomes in recipients. Second, RBCs inside the body have a lifespan of about 120 days, during which they are constantly metabolizing nutrients and releasing waste products that the kidneys, liver, and spleen filter. In a donor unit. RBCs are still undergoing metabolism and shedding waste products; however, the waste (e.g., hemolysate) accumulates in the donor blood bag. These detrimental substances include acids, potassium, hemoglobin, and iron, which are damaging outside of the RBCs; and pro-coagulant and pro-inflammatory microvesicles or microparticles. The accumulation of these byproducts lend to cell death causing the release of additional harmful substances. Consequently, concern has been raised about the safety of aging blood and the maximum shelf life of blood which is conventionally 42 days after being drawn in the U.S., while even shorter (35 days) in Europe.

Microparticles are fragments of cell membrane that house hemoglobin and pro-coagulatory and pro-inflammatory lipids. Excess potassium in the blood (i.e., hyperkalemia) is a risk for arrhythmias, particularly in sensitive populations, such as newborns. After the immediate life-threatening hyperkalemia and immune-mediated anaphylaxis, free hemoglobin and iron are the next most-recognized components to cause complications during transfusion. Thus, systems have evolved to capture and remove both cell-free hemoglobin and iron. However, the efficacy of these systems varies largely by individual and can be saturated. In fact, neonatal transfusionists commonly wash blood before transfusion into newborns, whose protective systems are under-developed and can be easily saturated, especially in the absence of "fresh" blood, Free hemoglobin rapidly consumes nitric oxide (NO), a molecule with many important roles in maintaining vascular homeostasis. NO is a vasodilator that inhibits platelet aggregation and controls inflammation and mitochondrial function. Thus, free hemoglobin scavenging of NO leads to acutely increased blood pressure, platelet aggregation, and inflammation. Free iron can also be damaging due to numerous iron catalyzing oxidative reactions, which form free radicals and other oxidants that enhance inflammation and cause cell and tissue damage. Additionally, free iron enhances clot formation and bacterial growth.

The above-described mediators of complications, whether antibodies or bioactive byproducts such as hemoglobin or microparticles, are located in the plasma component. Washing cells has been a way to reduce these side effects. However, washing requires centrifugation of cells, removal of plasma/storage solution, and addition of a new buffer, with this process being repeated two or more times. This process requires anywhere from 30 to 120 minutes, which is unacceptable in certain clinical scenarios. Additionally, washing can damage RBCs through repeated centrifugation at or above approximately 1,000 times the force of gravity, as is done clinically, causing additional hemoglobin release.

There are differences between young RBCs and old RBCs. For example, as a RBC ages, it progressively becomes more adhesive, and it loses negatively-charged surface molecules and volume. Transfused young RBCs last in the circulation longer than old RBCs. However, washing donor blood does not distinguish old RBCs from young RBCs. The current minimum for RBCs survival 24 hours after transfusion is approximately 75%. The destruction of old RBCs after transfusion contributes to saturation of the iron-binding capacity of the plasma, resulting in circulating free iron.

Conventional filtration products are available to treat whole blood, blood cells, or blood components. However, these conventional products do not address the specific challenge of improving the quality of packaged red blood cells after prolonged storage in order to make the RBCs more suitable for transfusion. Therefore, there is a need to extend the useful life and quality of donor RBC units, and a faster alternative to washing aged, stored RBCs to remove potentially harmful components from stored donor units without the need for repeated, time-consuming cycles of centrifugation and washing that can also lead to RBC damage.

SUMMARY

Some embodiments of the invention provide a gravity-fed blood purifier device fur removing waste particles from red blood cells. In one embodiment, a housing component has an inlet configured to provide unpurified RBCs into the housing component and an outlet configured to expel purified RBCs from the housing component. The housing component has an exit port configured to drain waste particles. Inside the housing component is a porous component having pores sized to allow waste particles to pass but to prevent healthy red blood cells from passing through the porous component. An electrode is connected to the porous component and configured to generate a negative potential across the porous component causing it to repel RBCs. The porous component is positioned such that the waste particles pass through pores of the porous component to the exit port and the purified RBCs are repelled by the porous component and expelled through the outlet In another embodiment, a gravity-fed blood purifier device can include a first end plate, a second end plate, and a first cylindrical tube positioned between the first end plate and the second end plate. The blood purifier device can also include a porous tube contained within the space defined by the first cylindrical tube. An inlet is configured to provide unpurified red blood cells into the space defined by the first cylindrical tube. An electrode can generate a negative potential across the porous tube to repel RBCs so that the purified RBCs exit through an outlet coupled to the second end plate.

In another embodiment, a gravity-fed blood purifier device for removing waste particles from red blood cells can include a first plate having, an inlet configured to provide unpurified red blood cells, a second plate coupled to the first plate, and a porous sheet coupled between the first plate and the second plate. An electrode is configured to generate a negative potential across the porous sheet to repel red blood cells, causing the waste particles to pass through pores of the porous sheet and the purified red blood cells to pass adjacent to the porous sheet. An outlet is also coupled to the first plate and is configured to receive the purified red blood cells repelled by the porous sheet.

These and other features, aspects, and advantages of the present invention will become better understood upon consideration of the following detailed description, drawings, and appended claims.

BRIEF DESCRIPTION OF THE DRAWINGS

FIG. 5 is a side perspective view of the blood purifier device of

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including" "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings, Further, "connected" and "coupled" are not restricted, to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing, from embodiments of the invention. Thus, embodiments of the invention are not intended to be limited to embodiments shown, but are to he accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

FIGS. 1-4 and 11 illustrate a blood purifier device 100 for red blood cells (RBCs). In some embodiments, the blood purifier device 100 is used in-line, at the point of care, rather than relying on conventional centrifugation according to one embodiment of the invention. The blood purifier device generally comprises a housing component configured to receive and hold RBCs during the filtration process described herein. The housing component has an inlet configured to provide unpurified RBCs into the housing component and an outlet configured to expel purified RBCs from the housing component. The housing component also has an exit port configured to drain waste particles out of the housing component. Inside the housing component is a porous component having pores sized to allow waste particles to pass but to prevent healthy red blood cells from passing through the porous component. An electrode is connected to the porous component and configured to generate a negative potential across the porous component causing it to repel RBCs. The porous component is positioned such that the waste particles pass through pores of the porous component to the exit port and the purified RBCs are repelled by the porous component and expelled through the outlet.

FIGS. 1-6 and 10-14 provide exemplary embodiments of the blood purifier device 100, 200, and 300. It is contemplated that the housing component and porous component may be formed of any suitable material, such as metal, stainless steel, ceramic, plastic, or the like, and may also take any shape and size required by the specific application of the present invention.

Figure 1:
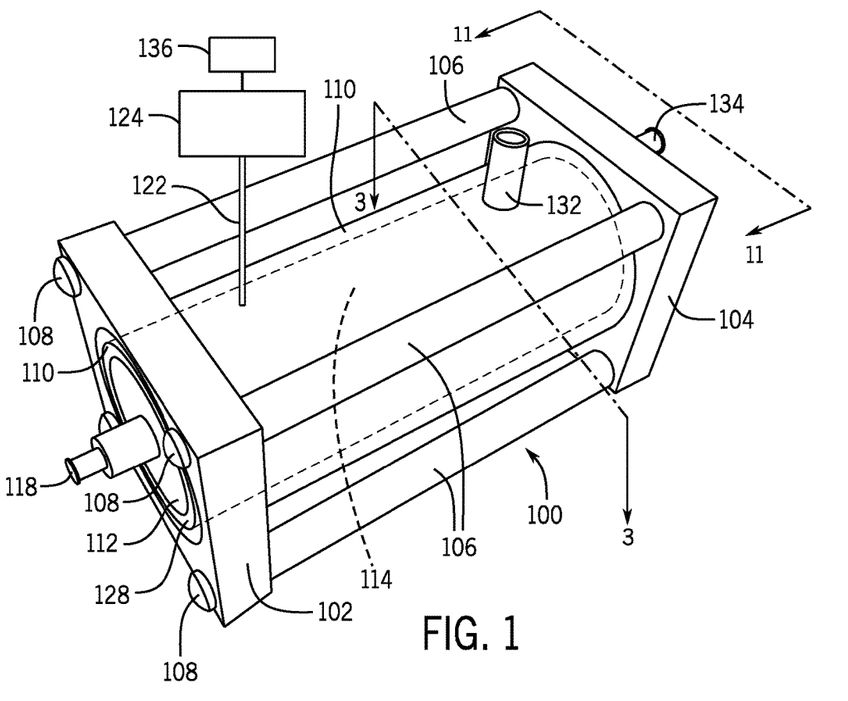
FIG. 1 is a perspective view of a blood purifier device according to one embodiment of the invention.
Figure 2:
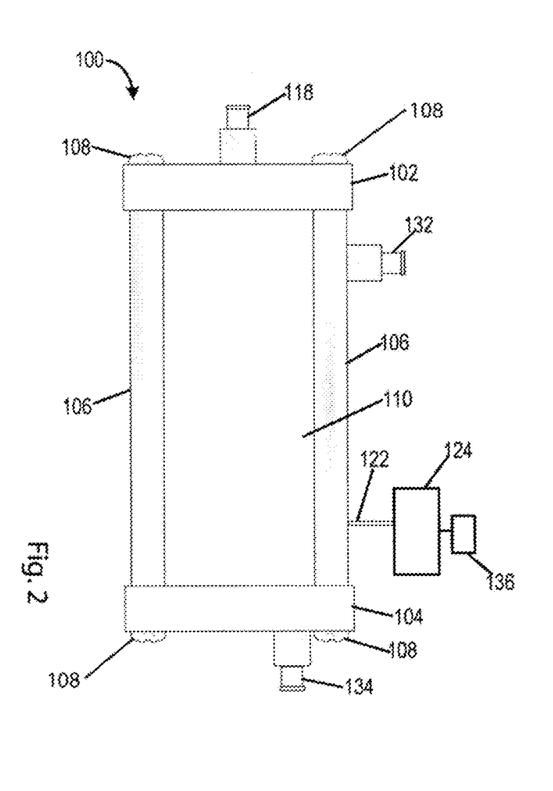
FIG. 2 is a side view of the blood purifier device of FIG. 1.
Figure 3:
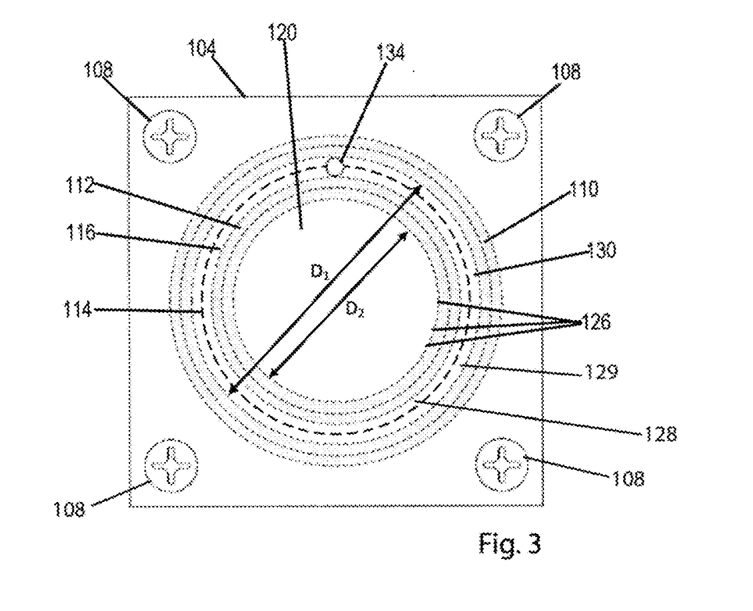
FIG. 3 is a crass-sectional view of the blood purifier device of FIG. 1 along 3-3.

The blood purifier device 100 can include a first end plate 102 and a second end plate 104 coupled together by a plurality of rods 106, Fasteners 108, for example screws, can be used to couple the plurality of rods 106 to the first end plate 102 and the second end plate 104. A first cylindrical tube 110 can extend between the first end plate 102 and the second end plate 104, and a second cylindrical tube 112 can be positioned inside the first cylindrical tube 110. A porous tube 114 can be positioned around an outer surface of the second cylindrical tube 112, as shown in FIG. 3, and within the first cylindrical tube 110. The porous tube 114 can be semi-impermeable so that it is impermeable to large cells and permeable to waste particles (e.g., hemolysate). An inlet 118 be coupled to the first end plate 102 to facilitate the flow of unpurified red blood cells into an interior space 120 defined by an interior of the second cylindrical tube 112. An electrode 122 can be coupled to a voltage source 124 to generate a negative charge across the porous tube 114. The negative potential attracts waste particles suspended with the RBCs and repels the RBCs. Thus, unpurified RBCs pass through perforations 126, as shown in FIG. 3, of the second cylindrical tube 112 into a space 128. However, the purified RBCs do not pass through the semi-impermeable porous tube 114. The space 128 can be defined by the outer surface 116 of the second cylindrical tube 112 and the porous tube 114. A space 129 can be defined by the porous tube 114 and an inside surface 130 of the first cylindrical tube 110. The RBCs pass adjacent to the porous tube 114. An exit port 132, as shown in FIG. 1, can be coupled perpendicular to the first cylindrical tube 110 to allow the waste particles (e.g., hemolysate, alloantibodies) from the donor unit to drain from the blood purifier device 100. The exit port 132 may extend from an upper portion of the first cylindrical tube 110 and be directed upward as shown in the embodiment of FIG. 2. In other embodiments, the exit port 132 may extend from any portion of the first cylindrical tube 110 and may exit at any angle. The purified RBCs, on the other hand, can exit the blood purifier device 100 through an outlet 134, e.g., coupled to the second end plate 104, that connects the space 128 to the exterior of the blood purifier device.

Figure 11:
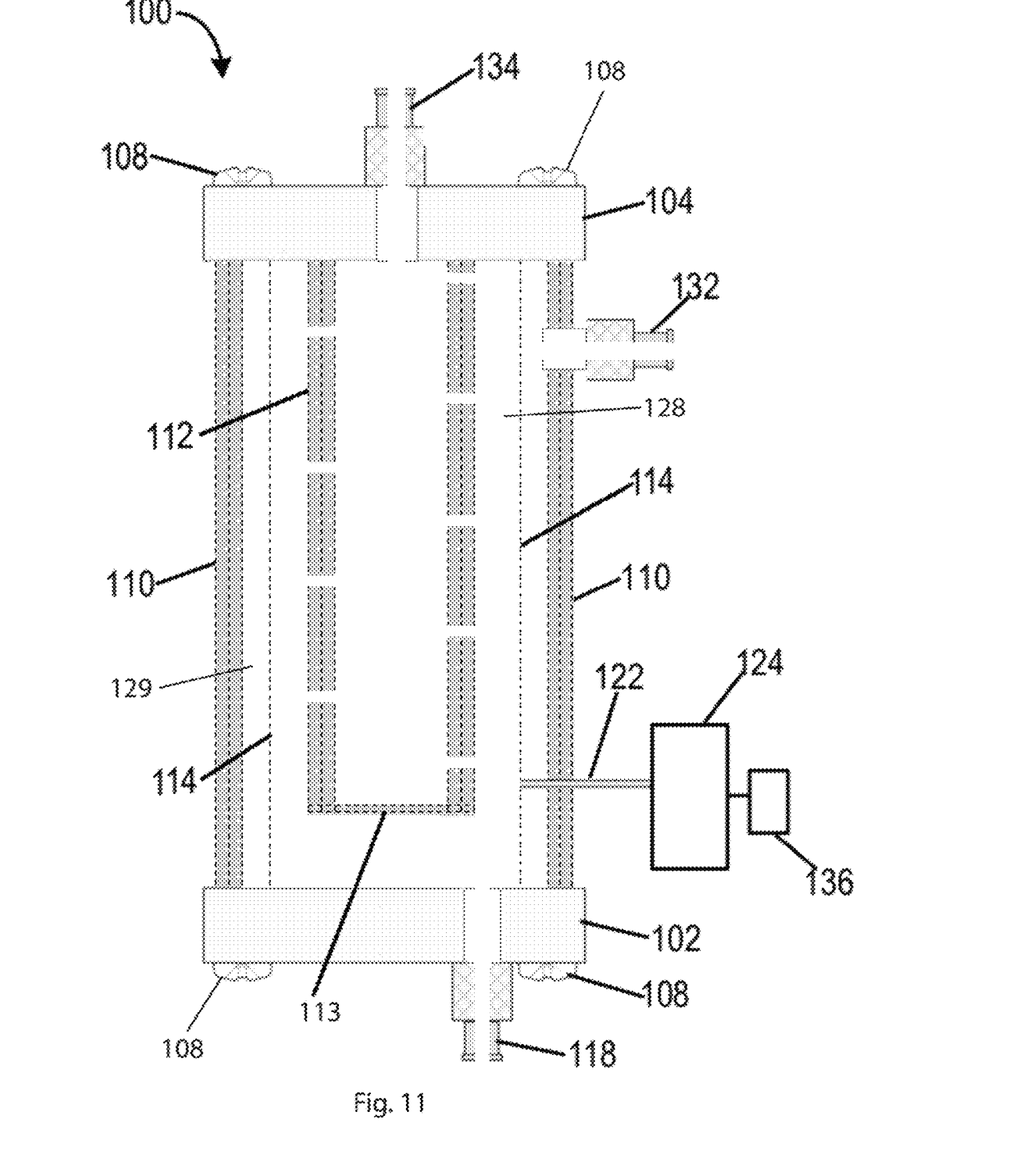
FIG. 11 is a cross sectional view of the blood purifier of FIG. 1 along 11-11.

As shown in FIGS. 2, 3, and 11 the first end plate 102 and the second end plate 104 can he substantially square in shape and have dimensions of about 2.5 inches by 2.5 inches. The first end plate 102 and the second end plate 104 can be constructed from, but not limited to, a polycarbonate, polypropylene, or polyethylene material, for example. The plurality of rods 106 can be cylindrically shaped and constructed of aluminum, for example. However, any suitable shape or material can he used for the rods 106 to connect the first end plate 102 and the second end plate 104.

Still referring to FIGS. 2, 3, and 11, the first cylindrical tube 110 can have a first diameter $D_1$ between about 0.5 inches and about 4 inches, for example. In an alternative embodiment, the first diameter $D_1$ can be about 1.25 inches and about 1.5 inches. The first cylindrical tube 110 can be between about 2.0 inches and about 20 inches in length, thereby having a volume of about 6 to 4000 milliliters. The first cylindrical tube 110 can be constructed of but not limited to, any suitable material (such as transparent, plastic material) to allow a user to observe the purification process, as will be described below, using the blood purifier device 100.

Similarly, the second cylindrical tube 112, which is nested in the first cylindrical tube 110, can have second diameter between about 0.25 inches and about 3.5 inches, for example. In an alternative embodiment, the second diameter $D_2$ can be between about 0.75 inches and about 1 inch. The second cylindrical tube 112 can be between about 2.0 inches and about 20 inches in length, thereby having a volume of about 1.5 to 3150 milliliters. It should be known to one skilled in the art that the dimensions of the first cylindrical tube and second cylindrical tube may he any dimension. The second cylindrical tube 112 can be constructed of but not limited to, any suitable material (such as transparent or translucent, plastic to allow a user to observe the purification process), using the blood purifier device 100. In addition, the second cylindrical tube can include perforations 126 to facilitate the purified RBCs to pass through the second cylindrical tube 112 into the space 128 defined between the porous tube 114 and the second cylindrical tube 112, as shown in FIGS. 3 and 11. Alternatively, the second cylindrical tube 112 can be excluded from the blood purifier device 100 since the second cylindrical tube 112 mainly provides mixing and turbulence of the RBCs. Furthermore, as exemplified in FIG. 11, the second cylindrical tube 112 may comprise an end 113. The end 113 may be located at the first end plate 102 or at some distance between the first end plate 102 and the second end plate 104. Alternately, the second cylindrical tube 112 extends from the first end plate 102 to the second end plate 104 and does not include an end plate 113.

In one embodiment, the porous tube 114 can be positioned around the outer surface 130 of the second cylindrical tube 112. In other embodiments, such as that shown in FIG. 11, the porous tube 114 can be positioned at some point between the first cylindrical tube 110 and the second cylindrical tube 112. Further, in various embodiments the porous tube 114 may be positioned any where between the first cylindrical tube 110 and the second cylindrical tube 112 and may be held in place by the first cylindrical tube 110 and/or the second cylindrical tube 112. The porous tube 114 can be made from a stainless steel mesh or any suitable chargeable material having pores sized between about 0.1 microns and about 2 microns, for example. Through the micron pores of the porous tube 114, suspensions of unpurified RBCs are purified by gravity filtration. Additionally, a static, negative charge provided by the voltage source 124 and electrode 122 can be applied to the porous tube 114 to repel RBCs and attract waste particles. The waste particles can be hemolysate, for example, including hemoglobin, cell-free hemoglobin, microparticles and potassium, or residual donor plasma, including alloantibodies.

Figure 10:
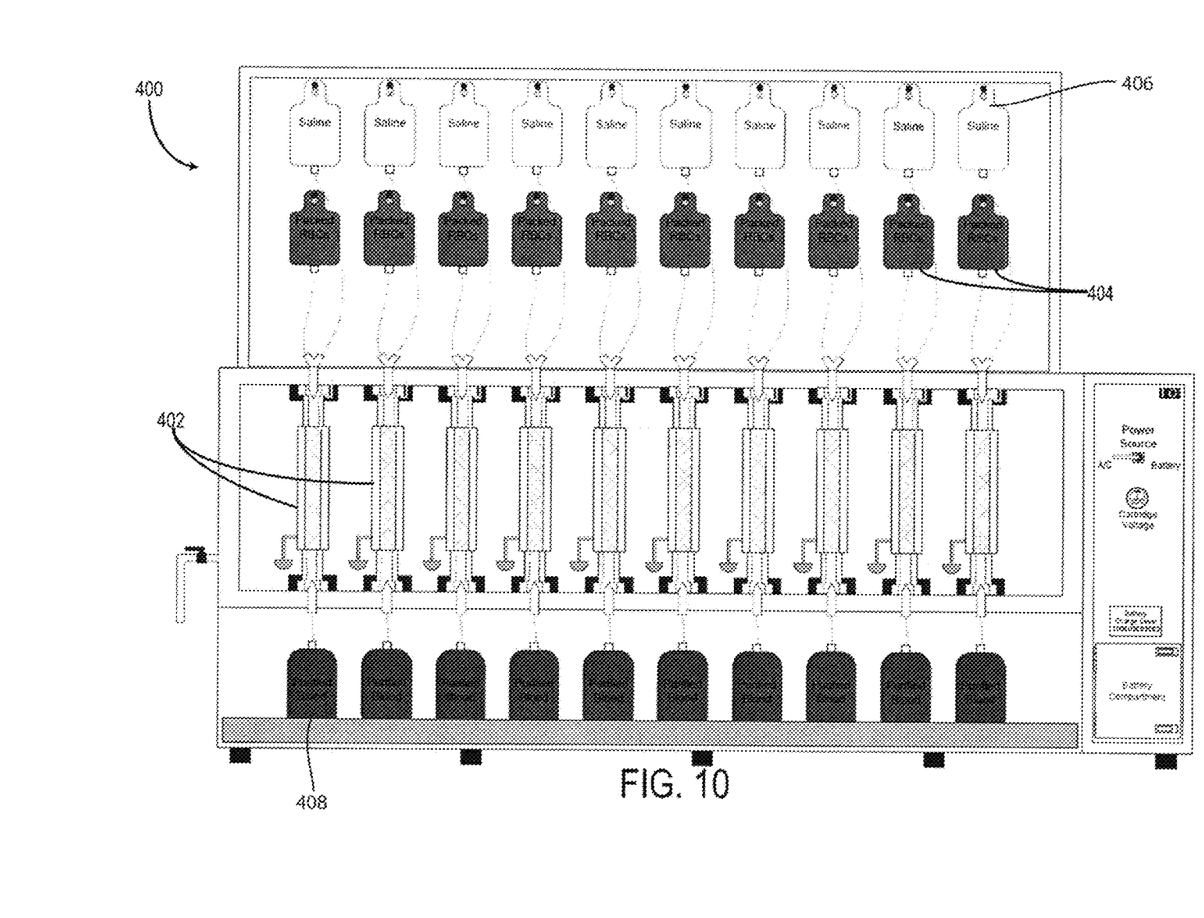
FIG. 10 is a side view of a multi-unit blood, purifier device according to another embodiment of the invention.

The voltage source 124 can be a conventional 9 volt battery, a solar panel, a 9 volt to 24 volt DC power supply, or any suitable voltage source that can apply a substantial voltage to repel RBCs. Alternatively, a hand crank can be used to provide a negative charge across the porous tube 114, and an indicator 136 can be provided, as shown in FIG. 1, to indicate appropriate charge has been supplied to the porous tube 114. A standard AC power wall outlet with an AC to DC transformer can also be used to supply the DC voltage, for example. In yet another alternative, a negatively charged surface can be prepared through other means, for example, by applying an anionic dopant to the porous tube 114. In yet another alternative, as shown in FIG. 10, a multiple blood purifier system 400 can include a plurality of cartridges 402 in automated, multichannel instruments configured to purify multiple units of red blood cells 404 simultaneously. Each cartridge 402 contains a blood purifier device, such as the blood purifier device embodiments 100, 200, and 300 described herein, and is configured to process unit(s) of RBCs 404. Moreover, the each cartridge 402 may receive saline from saline unit(s) 406. As shown in the embodiment of FIG. 10, the saline and RBCs may be combined at a point in the system 400 prior to entering the cartridge 402. In another embodiment, the saline and RBCs may both feed into the cartridge 402 via separate inlet ports, and the saline and the RBCs may combine and mix inside the cartridge 402. The cartridge 402 outputs purified, or cleaned, RBCs, which may be captured in containers to create purified blood units 408.

The above-described blood purifier device 100 can remove toxic compounds from expired units of blood, for example, in substantially less time required to wash the blood units by conventional means. The blood purifier device 100 relies on the size and charge differences between young RBCs, aged RBCs, and some of the harmful by-products (i.e., waste products) that accumulate over time in stored blood. The difference in surface charge and size is therefore utilized to remove the oldest (i.e., smallest and most positively-charged) RBCs while delivering the younger (i.e., larger and more negatively-charged) RBCs.

Figure 7:
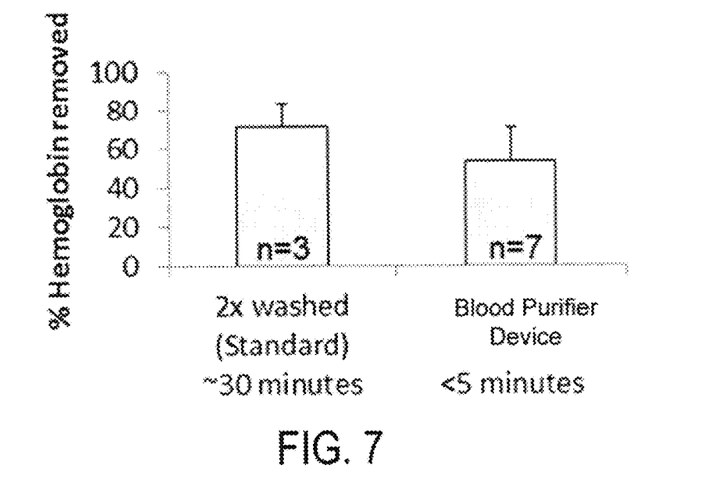
FIG. 7 is a graph showing a percentage of hemoglobin removed during conventional washing compared to the blood purifier device.

The blood purifier device 100 can also reduce the levels of harmful cell-free hemoglobin, microparticles, and possibly older RBCs in expired blood to levels equal to or better than obtained by washing, as shown in FIG. 7. The graph shown in FIG. 7 further shows that the purification of expired blood with the blood purifier device 100 can result M approximately a 51% decrease in free hemoglobin compared with control plasma (N=7). This is comparable to approximately a 71% decrease with conventional washing (N=3). This can be achieved in as few as 5 minutes, compared to the 30-120 minutes necessary for conventional washing. Additionally, compared to a control, the RBCs that pass through the blood purifier device 100 can have more resilience to lysis, consistent with younger RBCs passing over the porous tube 114, while removing older, lysis-prone RBCs.

Referring now to FIG. 2, during operation, saline (e.g., about one to five times the volume) and (expired, i.e. older than 42 days) blood can be passively mixed to provide unpurified RBCs to the blood purifier device 100. The unpurified RBCs can be gravity-fed through the inlet 118 into the interior space 120, as shown in FIG. 3, of the second cylindrical tube 112. The porous tube 114, as shown in FIG. 3, can then be charged by the voltage source 124 and the electrode 122. As previously described, the static, negative charge provided by the voltage source 124 and the electrode 122 repels RBCs. The waste particles can exit the blood purifier device 100 through the exit port 132, while the RBCs pass through the perforations 126 of the second cylindrical tube 112, but not through the porous tube 114 into the space 129, as shown in FIGS. 3 and 11. Thus, as waste particles exit the blood purifier device 100 through the exit port 132, purified or partially purified RBCs enter space 128 and can exit the blood purifier device 100 through the outlet 134. In this way, the RBCs are maintained within the porous tube 114. The purified or partially-purified RBCs exit through the exit port 132 as the amount of purified or partially-purified RBCs increases near the exit port 132. The accumulation of purified or partially-purified RBCs may increase pressure in the blood purifier device 100 or cause the RBCs to "climb" one another allowing the purified or partially-purified RBCs to exit the blood purifier device 100.

Figure 8:
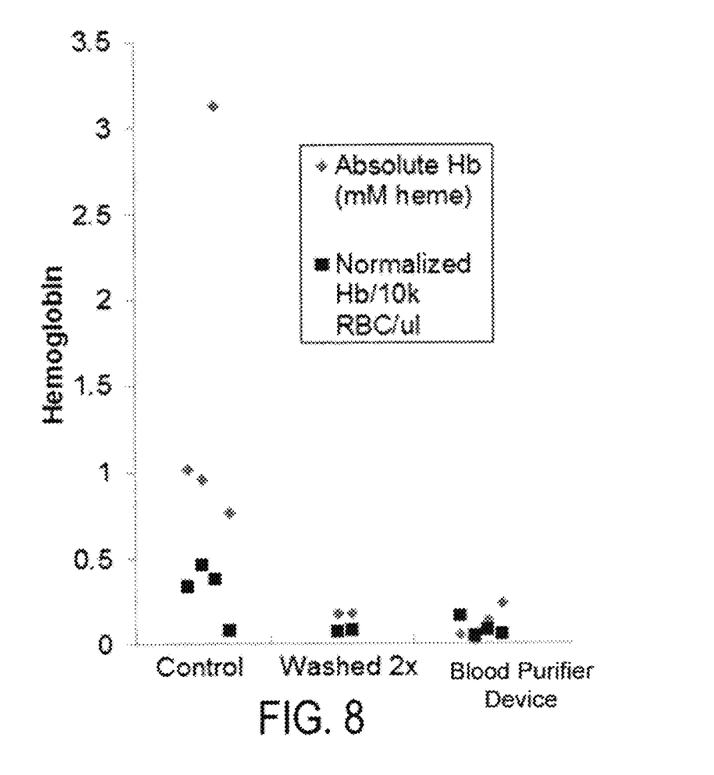
FIG. 8 is a graph showing hemoglobin concentration as determined by UV/VIS spectroscopy, both absolute hemoglobin (in mM heme) and hemoglobin normalized to RBCs for control, washed and purified using the blood purifier device.
Figure 9:
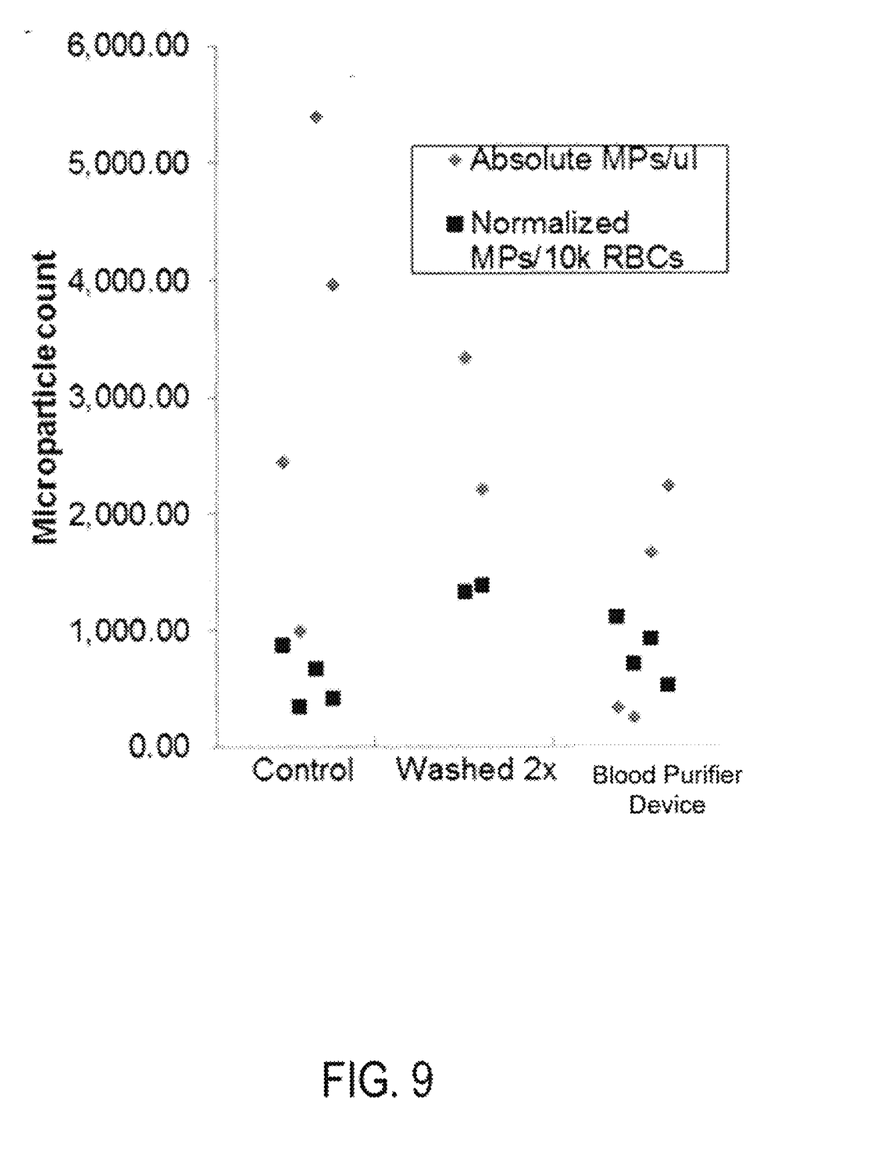
FIG. 9 is a graph showing a microparticle count of control, washed and purified samples using the blood purifier device.

To test the performance of the blood purifier device 100, purified RBCs can be analyzed using UV-visible spectroscopy to measure cell-free oxy-hemoglobin concentrations. For example, an Agilent 8453 UV/VIS spectrophotometer can be used to obtain this measurement, as shown in FIG. 8, which displays the hemoglobin concentration as determined by U V-visible spectroscopy, both absolute hemoglobin On mM heme) and hemoglobin normalized to RBCs. In addition, flow cytometry can be used to to examine microparticle content of the control, washed and purified samples using the blood purifier device 100. For example, as shown in FIG. 9, the microparticle count, both absolute (MPs/ul) and relative normalized to RBCs, for the control, washed, and purified samples using the blood purifier device 100 are shown. The purified RBCs can then be delivered to a patient in need of RBCs, at the point of use.

Alternatively, the blood purifier device 100 can be used in hospitals or blood banks, for example, or as previously described, placed in-line with units of blood being transfused in emergency or operating rooms to control hemolysate and residual donor plasma in-line at the point of care. Also, the blood purifier device 100 can be incorporated as an add-on, for example, to blood heaters, pumps, heart-lung machines or dialysis machines, as elevated levels of circulating microparticles and other detrimental byproducts are associated with mechanical manipulation of blood. In various embodiments, the blood, purifier device 100 can be any one or more of light-weight, single-use, sterile, disposable, durable, have a long shelf-life, and would not require expensive equipment or reagents to use.

Figure 4:
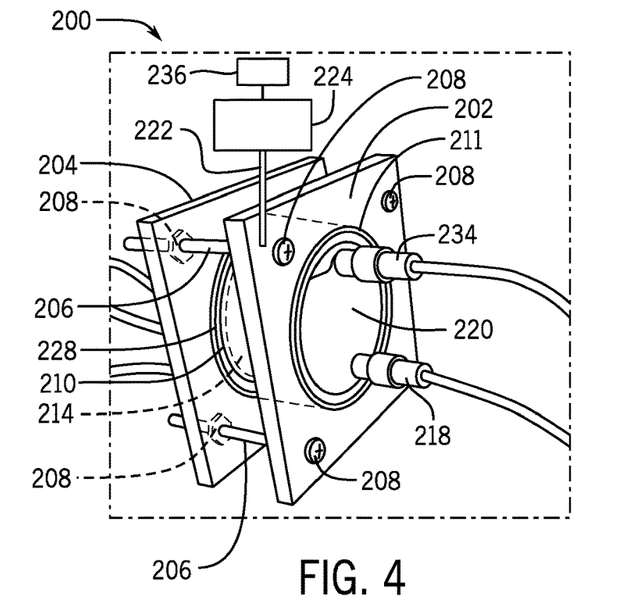
FIG. 4 is a side perspective view of a blood purifier device according to another embodiment of the invention.
Figure 5:
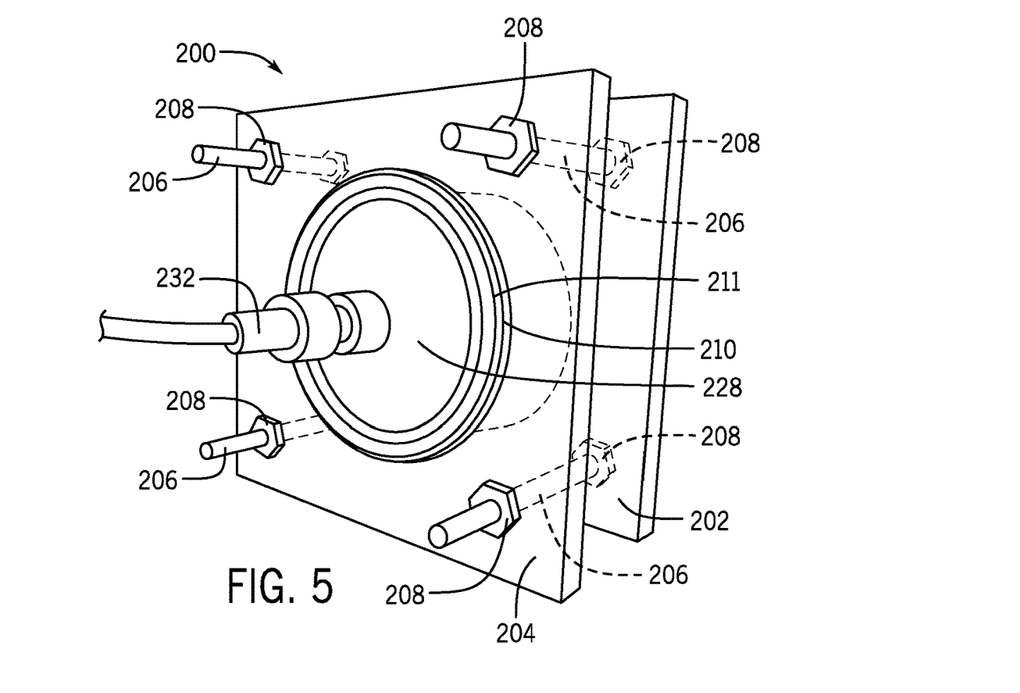
Figure 14:
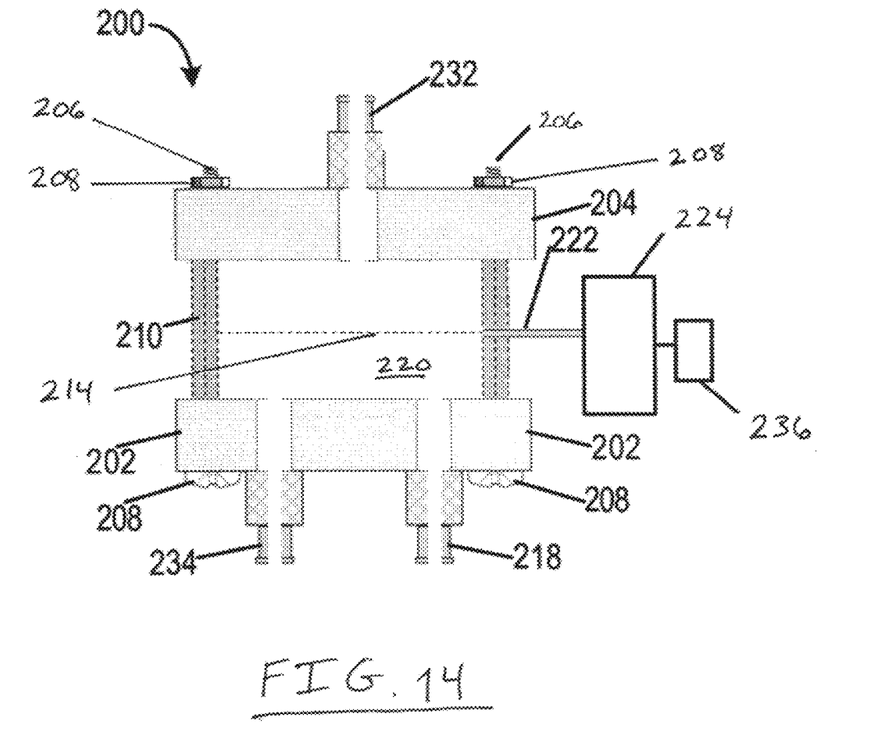
FIG. 14 is a cross section view of the blood purifier of FIGS. 4.

FIGS. 4, 5, and 14 illustrate an alternative embodiment of a blood purifier device 200. Similar reference numerals for corresponding elements will be used in reference to the blood purifier device 100. The blood purifier device 200 can include a first end plate 202 and a second end plate 204 coupled together by a plurality of rods 206. Fasteners 208, for example nuts and bolts, cart be used to couple the first end plate 202 and the second end plate 204. A first cylindrical tube 210 can extend between the first end plate 202 and the second end plate 204. A porous sheet 214 can be positioned within the first cylindrical tube 210 between the first end plate 202 and the second end plate 204 and held in place by o-rings 211, for example, as shown in FIG. 5. An inlet 218 can be coupled to the first end plate 202 to facilitate the flow of unpurified red blood cells into an interior space 220 defined by the first cylindrical tube 210. An electrode 222 can be coupled to a battery 224, for example, to generate a negative potential across the porous sheet 214. The negative charge repels RBCs. Thus, waste passes through the porous sheet 214 into a space contiguous with exit port 232 defined by the porous sheet 214 and the second end plate 204 to allow the waste particles from the RBCs to drain from the blood purifier device 200. The purified RBCs, on the other hand, can exit the blood purifier device 200 through an outlet 234 coupled to the first end plate 202 that connects the interior space 220 to atmosphere. The embodiment shown in FIGS. 4, 5, and 14 can use a digital multimeter, for example, to ensure proper electrical connections to the electrode.

Still referring to FIGS. 4, 5, and 14, the first end plate 202 and the second end plate 204 can be substantially square in shape and have dimensions of about 2.5 inches by 2.5 inches. The first end plate 202 and the second end plate 204 can be constructed from, but not limited to, a polycarbonate, polypropylene, or polyethylene material, for example. The plurality of rods 206 can be cylindrically shaped and constructed of aluminum, for example. However, any suitable shape or material can be used for the rods 206 to connect the first end plate 202 and the second end plate 204, as well as end plates.

The first cylindrical tube 210, as shown in FIGS. 4, 5, and 14, can have a first diameter $D_1$ between about 1.7 inches and about 2.1 inches, for example. In an alternative embodiment, the first diameter $D_1$ can be between about 1.25 inches and about 1.5 inches. The first cylindrical tube 210 can be between about 0.5 inches and about 1 inch in length, thereby having a volume of about 50 to 60 milliliters. The first cylindrical tube 210 can be constructed of, but not limited to any suitable transparent or translucent, plastic material to allow a user to observe the purification process using the blood purifier device 200.

The porous sheet 214 can be made from a stainless steel mesh or any suitable chargeable material having micron pore sizes between about 0.1 micron and about 2 microns, for example. Through micron pores of the porous sheet 214, suspensions of unpurified RBCs are purified by gravity filtration. Additionally, a static, negative charge provided by the voltage source 224 and electrode 222 can be applied to the porous sheet 214 to repel RBCs. An indicator 236 can also be provided to indicate appropriate charge has been supplied to the porous sheet 214. The waste particles can be hemolysate, for example, including hemoglobin, cell-free hemoglobin, microparticles and potassium, or residual donor plasma, including alloantibodies.

The above-described blood purifier device 200 can remove toxic compounds from expired units of blood, for example, in substantially less time than is required to wash the blood units by conventional means. The blood purifier device 200 relies on the size and charge differences between young RBCs, aged RBCs, and some of the harmful by-products (i.e., waste products) that accumulate over time in stored blood. The difference in surface charge and size is therefore utilized to remove the oldest (i.e., smallest and most positively-charged) RBCs while delivering the younger (i.e., larger and more negatively-charged) RBCs. The blood purifier device 200 can also reduce the levels of harmful cell-free hemoglobin, microparticles, and possibly older RBCs in expired blood to levels equal to or better than obtained by washing.

Still referring to FIGS. 4, 5, and 14, during operation, saline (e.g., about one to five times the volume) and blood (including expired blood, i.e., older than 42 days) can be passively mixed to provide unpurified RBCs to the blood purifier device 200. The unpurified RBCs can be gravity-fed through the inlet 218 into the interior space 220 of the first cylindrical tube 210. The inlet 218 is positioned below the outlet 234. The porous sheet 214 can then be charged by the battery and electrode to repel RBCs. The waste particles can travel through the porous sheet 214 to exit the blood purifier device 200 through the exit port 232, while the RBCs are repelled by the porous sheet 214 and stay on the inlet side of the porous sheet 214 and can exit the blood purifier device through the outlet 234 as purified RBCs. In this way, the purified RBCs pass adjacent to the porous sheet. The purified RBCs can then be delivered to a patient in need of RBCs, at the point, of use, for example.

Figure 6:
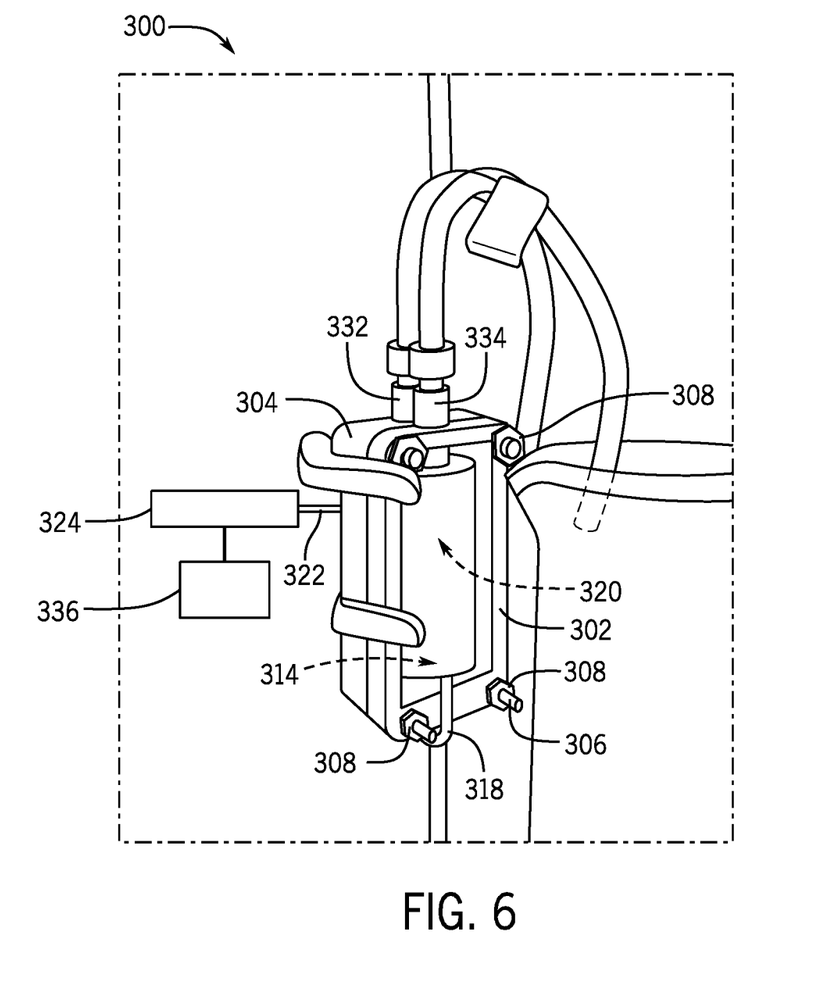
FIG. 6 is a perspective view of a blood purifier device according to another embodiment of the invention.
Figure 13:
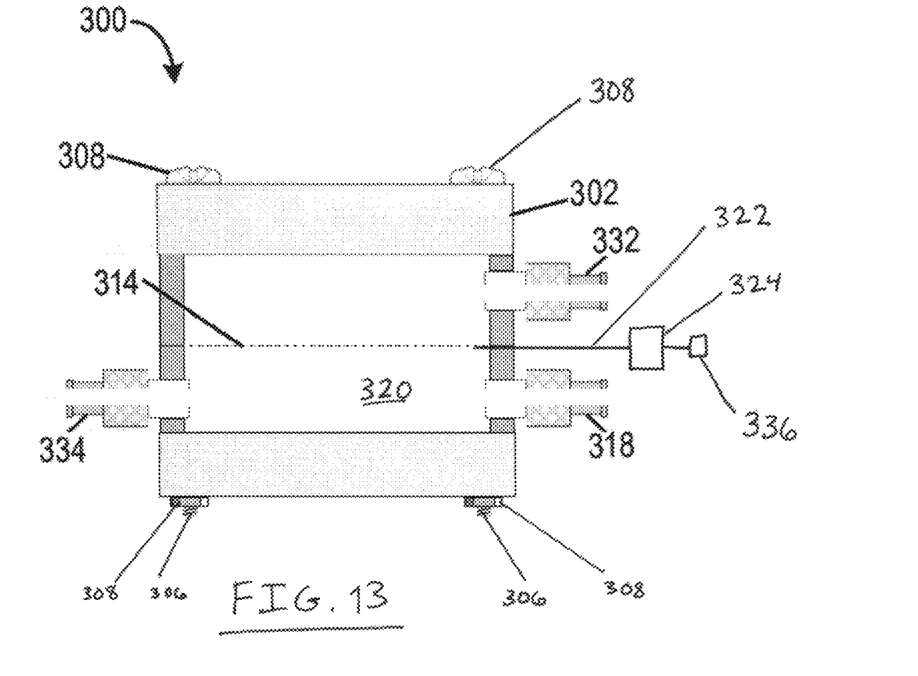
FIG. 13 is a cross section view of the blood purifier of FIG. 6

FIGS. 6 and 13 illustrate an alternative embodiment of a blood, purifier device 300. Similar reference numerals for corresponding elements will be used in reference to the blood purifier devices 100 and 200. The blood purifier device 300 can include a first end plate 302 and a second end plate 304 coupled together by a plurality of rods 306. Fasteners 308, for example nuts, can be used to couple the plurality of rods 306 to the first end plate 302 and the second end plate 304. A porous sheet 314 can be positioned between the first end plate 302 and the second end plate 304 with less than about 1 mm (and up to about 4 mm) of space between the porous sheet 314 and the first end plate 302 and the second end plate 304, for example. An inlet 318 can be coupled to the first end plate 302 to facilitate the flow of unpurified red blood cells into an interior space 320 defined within the first end plate 102. An electrode 322 can be coupled to a battery 324, for example, to generate a negative potential across the porous sheet 314. An indicator 336 can also be provided. The negative potential repels RBCs. Thus, waste particles pass through the porous sheet 314 and the purified RBCs remain in the interior space 320. An exit port 332 can be coupled to the second end plate 304 to allow the waste particles from the RBCs to drain from the blood purifier device 300. The purified RBCs, on the other hand, can exit the blood purifier device 300 through an outlet 334 coupled to the first end plate 302 that connects the interior space 320 to atmosphere.

Still referring to FIGS. 6 and 13, the first end plate 304 can be substantially rectangular in shape and have dimensions of about 1 inch by 4 inches. The first end plate 302 and the second end plate 304 can be constructed from, but not limited to, a polycarbonate, polypropylene, or polyethylene material, for example. The plurality of rods 306 can be cylindrically shaped and constructed of aluminum, for example. However, any suitable shape or material can be used for the rods 306 to connect the first end plate 302 and the second end plate 304.

The porous sheet 314 can be made from a stainless steel, such as a stainless steel mesh, or any suitable chargeable material having micron pore sizes between about 0.1 micron and about 2 microns, for example. Through micron pores of the porous sheet 314, suspensions of unpurified RBCs are purified by gravity filtration. Additionally, a static, negative charge provided by the battery 324 and electrode 322 can be applied to the porous sheet 314 to repel RBCs. The waste particles can be, for example, microparticles including hemoglobin, cell-free hemoglobin and potassium.

During, operation, saline (e.g., about one to five times the volume) and blood (including expired units, i.e., older than 42 days) can be passively mixed to provide unpurified RBCs to the blood purifier device 300. The unpurified RBCs can be gravity-fed through the inlet 318 into the interior space 320 of the first end plate 302. The porous sheet 314 can then be charged by the battery 324 and electrode 322 to repel RBCs. The waste particles can exit the blood purifier device 300 through the exit port 332, while the RBCs pass adjacent the porous sheet 314 and can exit the blood purifier device through the outlet 334 as purified RBCs. The purified RBCs can then be delivered to a patient in need of RBCs, at the point of use, for example.

Figure 12:
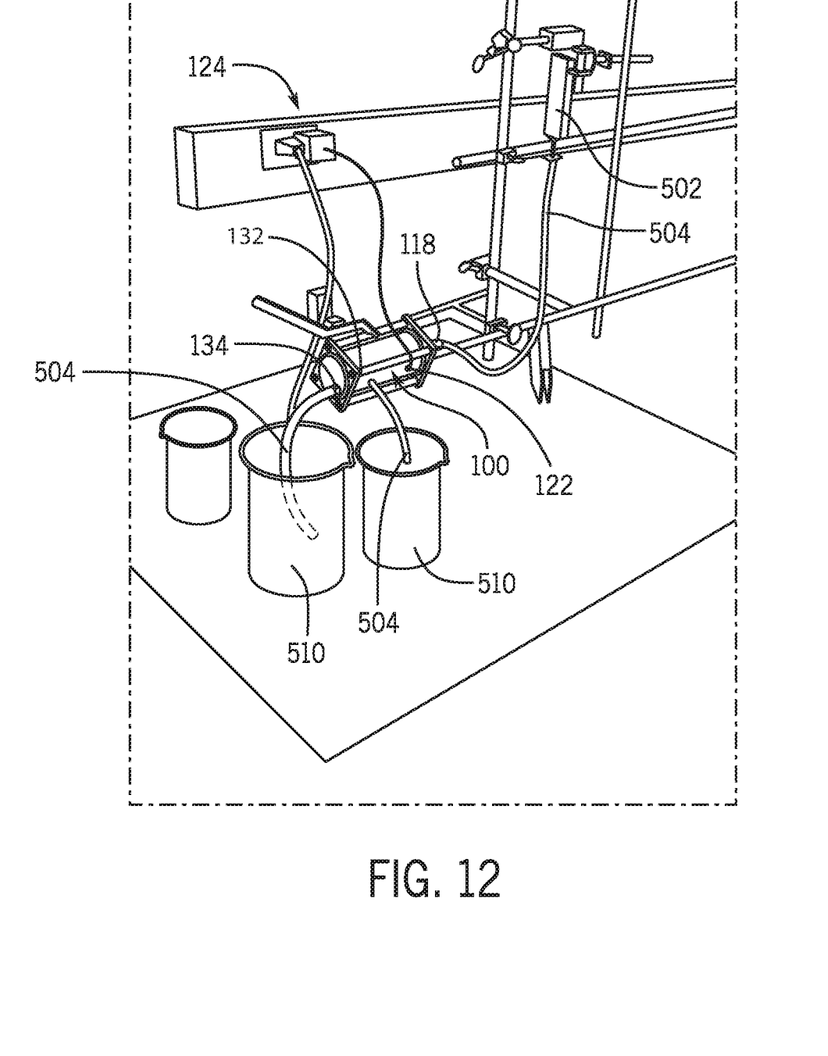
FIG. 12 is a perspective view of the blood purifier of FIG. 1 in a lab configuration.

Referring to FIG. 12, blood purifier device 100, as referenced in FIGS. 1-4 and 11, is shown in a lab configuration. It should be known to one skilled in the art that the blood purifier device 100 may be set into any configuration, including the configuration depicted in FIG. 10. The voltage source 124 may be an electrical wall outlet with a DC convertor. The voltage source 124 is connected to the electrode 122. An inlet 118 is connected to a flexible tubing 504 and the flexible tubing 504 is connected to a blood bag 502. In FIG. 12, the blood bag 502 and tubing 504 is shown to be a flexible plastic material, but the blood bag 502 and tubing, 504 may be made of any material including rigid material. Unpurified red blood cells in the blood bag travels through the tubing 504 by gravity and enters the blood purifier device 100 at the inlet 118. The unpurified RBCs may be only unpurified RBCs, unpurified RBCs in a saline solution, or any other combination of liquid with unpurified RBCs. It should also be known to one skilled in the art that a saline solution or other liquid may be added to the unpurified RBCs in the blood bag 504, along the tubing 502. within the porous tube 114, or in the blood purifier device 100 by way of a separate inlet (not shown). An exit port 132 is coupled to the first cylindrical tube 110 to allow waste particles from the RBCs to drain from the blood purifier device 100. A tubing 504 is connected to the exit port 132 to create a travel path away from the blood purifier device 100. A collection container 510 collects the waste. Similarly, an outlet 134 allows purified RBCs to exit the blood purifier device 100 and the outlet 134 is connected to a tubing 504.

The tubing 504 creates a travel path away from the blood purifier device 100. A collection container 510 collects the purified RBCs. It should be known by one skilled in the art that the collection container 510 may take any form and be made of any material. Also, the collection container 510 may be excluded from certain embodiments of the present invention so that purified RBCs may flow to its end user, such as a blood vein of a patient.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

We claim:

1. A gravity fed blood purifier device for removing waste particles from red blood cells, the blood purifier device comprising:
   a first end plate and a second end plate;
   a first cylindrical tube positioned between the first end plate and the second end plate;
   a porous tube positioned between the first end plate and the second end plate and within the first cylindrical tube;
   an inlet that provides unpurified red blood cells into the porous tube;
   an electrode and a voltage source configured to maintain a negative potential across the porous tube to repel red blood cells;
   wherein the blood purifier device is configured to cause the waste particles to pass through pores of the porous tube and the red blood cells to be maintained within the porous tube such that the waste particles are removed from the first cylindrical tube through an exit port and purified red blood cells are provided to an outlet during operation of the blood purifier device.

2. The blood purifier device of claim 1, and further comprising a second cylindrical tube having an outer surface and positioned inside the first cylindrical tube, wherein the porous tube is coupled to the outer surface of the second cylindrical tube between the second cylindrical tube and the first cylindrical tube.

3. The blood purifier device of claim 2, wherein the first cylindrical tube has a first diameter between about 0.5 inches and about 4.0 inches, and the second cylindrical tube has a second diameter between about 0.25 inches and about 3.5 inches, wherein the second diameter is smaller than the first diameter.

4. The blood purifier device of claim 1, wherein the pores of the porous tube are sized between about 0.1 micron and about 2 microns.

5. The blood purifier device of claim 4, wherein the porous tube is constructed of a stainless steel.

6. The blood purifier device of claim 1, wherein the red blood cells provided at the inlet are premixed with saline.

7. The blood purifier device of claim 1, further comprising a second inlet providing saline into the porous tube, wherein the saline mixes with the unpurified red blood cells within the porous tube.

8. The blood purifier device of claim 2, wherein the second cylindrical tube includes perforations for the unpurified red blood cells to pass through to the porous tube.

9. The blood purifier device of claim 1, wherein the waste particles include at least one of hemoglobin, cell-free hemoglobin, microparticles, microvesicles, potassium, residual donor plasma and alloantibodies.

10. The blood purifier device of claim 1, and further comprising an indicator to indicate when the porous tube is sufficiently charged by the electrode.

11. The blood purifier device of claim 1, wherein the electrode is coupled to at least one of a hand crank, a 9 volt battery, a solar panel and a 9 volt to 24 volt DC power supply to provide charge to the electrode.

12. The blood purifier device of claim 1, wherein at least one of the first end plate and the second end plate are constructed of at least one of a polycarbonate material, a polypropylene material, and a polyethylene material.

13. A gravity-fed blood purifier device for removing waste particles from red blood cells, the blood purifier device comprising:
   a first plate having an inlet configured to provide unpurified red blood cells;
   a second plate coupled to the first plate;
   a porous sheet coupled between the first plate and the second plate;
   an electrode and a voltage source configured to maintain a negative potential across the porous sheet to repel red blood cells;
   wherein the blood purifier device is configured to separate the waste particles from healthy red blood cells by causing the waste particles to pass through pores of the porous sheet to an exit port and the purified red blood cells to pass adjacent to the porous sheet to an outlet coupled to the first plate during operation of the blood purifier device.

14. The blood purifier device of claim 13, wherein the inlet is positioned near or below the outlet.

15. The blood purifier device of claim 13, wherein the pores of the porous sheet are sized between about 0.1 micron and about 2 microns.

16. The blood purifier device of claim 13, wherein the porous sheet is constructed of stainless steel.

17. The blood purifier device of claim 13, wherein the waste particles include at least one of hemoglobin, cell-free hemoglobin, microparticles, microvesicles, potassium, residual donor plasma and alloantibodies.

18. The blood purifier device of claim 13, further comprising the exit port in the second plate configured to drain the waste particles that pass through the porous sheet.

19. A gravity-fed blood purifier device for removing waste particles from red blood cells, the blood purifier device comprising:
   a housing component having
      an inlet configured to provide unpurified red blood cells into the housing component;
      an outlet configured to expel purified red blood cells from the housing component; and
      an exit port configured to drain waste particles out of the housing;
   a porous component inside the housing component; and
   an electrode and a voltage source configured to maintain a negative potential across the porous component to repel red blood cells;
   wherein the blood purifier device is configured to separate the waste particles from healthy red blood cells such that the waste particles pass through pores of the porous component to the exit port and the purified red blood cells are repelled by the porous component and expelled through the outlet during operation of the blood purifier device.

20. The blood purifier device of claim 19, wherein the inlet is positioned lower on the housing component than the outlet.

21. The blood purifier device of claim 19, wherein the pores of the porous component are sized between about 0.1 micron and about 2 microns.

* * * * *